(12) United States Patent  
Alper

(10) Patent No.: US 7,981,298 B2  
(45) Date of Patent: Jul. 19, 2011

(54) PROCESS FOR REMOVAL OF CONTAMINANTS FROM INDUSTRIAL STREAMS

(76) Inventor: Hal Alper, Flowery Branch, GA (US)

( * ) Notice: Subject to any disclaimer, the term of this patent is extended or adjusted under 35 U.S.C. 154(b) by 854 days.

(21) Appl. No.: 12/001,057

(22) Filed: Dec. 7, 2007

(65) Prior Publication Data

US 2008/0210635 A1    Sep. 4, 2008

Related U.S. Application Data

(60) Provisional application No. 60/874,915, filed on Dec. 14, 2006.

(51) Int. Cl.  
*C02F 1/28* (2006.01)  
*C02F 1/62* (2006.01)

(52) U.S. Cl. ........ 210/668; 210/688; 210/692; 210/694; 210/748.01

(58) Field of Classification Search .................... 210/914  
See application file for complete search history.

(56) References Cited

U.S. PATENT DOCUMENTS

| | | | |
|---|---|---|---|
| 2,107,945 A | 2/1938 | Hull et al. | |
| 4,154,704 A * | 5/1979 | Vinton et al. | 502/433 |
| 5,080,799 A * | 1/1992 | Yan | 210/661 |
| 5,292,412 A | 3/1994 | Pitton | |
| 6,117,333 A * | 9/2000 | Frankiewicz et al. | 210/705 |
| 6,180,010 B1 * | 1/2001 | Alper | 210/680 |
| 6,861,002 B2 | 3/2005 | Hughes | |
| 6,958,136 B2 | 10/2005 | Chandran et al. | |
| 7,041,222 B1 * | 5/2006 | Rainer | 210/660 |
| 7,211,707 B2 * | 5/2007 | Axtell et | 588/299 |
| 7,264,721 B2 * | 9/2007 | Alper | 210/315 |
| 7,264,722 B2 * | 9/2007 | Alper | 210/315 |
| 2002/0027105 A1 | 3/2002 | Alper | |

* cited by examiner

*Primary Examiner* — Peter A Hruskoci  
(74) *Attorney, Agent, or Firm* — Klauber & Jackson LLC

(57) ABSTRACT

A method and system for removing from an aqueous system which is contaminated therewith: (1) mercury present as colloids, ions and/or organically bound compounds, and (2) hydrocarbons solubilized, dispersed, and/or emulsified in the said system. Pursuant to the invention the aqueous system to be treated (such as "produced water") is passed successively through three filtration stages. The first filtration stage is provided with absorption media which effects reduction/removal of dispersed organically bound mercury species and of the dispersed and partially dissolved hydrocarbon phases, as well as of some colloidal mercury and other dissolved metallic species. The second filtration stage utilizes a salt modified reticulated granular filtration media for reduction/removal of slightly dissolved hydrocarbon phases, mercury in colloidal and ionic form and other dissolved metals. The third filtration stage is a polishing stage, which serves to further reduce by electroless or voltaic reduction residual elemental mercury and/or residual colloidal and ionic mercury. At this third stage metallic mercury is incorporated into a metallic matrix from which the mercury may preferably be recovered.

6 Claims, 4 Drawing Sheets

PROCESS FOR REMOVAL OF CONTAMINANTS FROM INDUSTRIAL STREAMS

RELATED APPLICATION

This application claims priority from U.S. provisional patent application Ser. No. 60/874,915, filed on Dec. 14, 2006.

FIELD OF INVENTION

This invention relates generally to methods and apparatus for removing contaminants from aqueous systems, and more specifically relates to filtration methods and devices for removing mercury and organic compounds from such aqueous systems.

BACKGROUND OF INVENTION

In the course of practicing a wide variety of commercially important industrial processes, aqueous process streams (or more generally "aqueous systems") are produced which are contaminated with pernicious quantities of mercury present as colloids, ions or organically bound compounds, and with hydrocarbons which are solubilized, dispersed, or emulsified in the aqueous system. The mercury contaminants have proved to be particularly difficult to remove or reduce to levels deemed harmless to humans. This is a problem that has reached very serious dimensions, in part because even where mercury may initially be present in low concentrations in sea water, the natural predator-prey relation in the oceanic food chain causes build up of mercury in the large fish species widely eaten by humans to a level where e.g. certain types of tuna are now considered unsafe for frequent human consumption, especially by women who are pregnant.

Generally similar concerns exist with respect to hydrocarbon contaminants. Many of these latter noxious contaminants are also among the more difficult compounds to remove from aqueous media. Most are carcinogenic, and yet such compounds must be removed or minimized before discharge of the industrial stream in which they may be present in order to environmentally protect the bodies of water which the discharges eventually reach.

One type of such hydrocarbon contaminant consists of dispersed oils, which are often present as oil-in-water emulsions. A further source of contamination arises from presence in the water of pernicious slightly soluble organic compounds such as benzene, toluene, xylene, halogenated hydrocarbons, ethoxylated glycols, etc.

In the present inventor's U.S. Pat. No. 6,180,010 it is disclosed that the compositions described in the inventor's U.S. Pat. Nos. 5,437,793; 5,698,139; 5,837,146; and 5,961,823, (all of which disclosures are hereby incorporated by reference) have extremely strong affinities for the aforementioned contaminants in water; and that when aqueous streams containing these noxious contaminants are passed through filtration media incorporating these compositions, the contaminants are immobilized at the media, as a result of which concentration levels of the contaminants in the filtrate may be reduced to very low values. The principles of these earlier inventions are also applied in the present invention, but in a synergistic combination with further contaminant removal methodology.

An important example of the type of operation to which the present invention is directed arises in the operation of oil and gas exploration and drilling facilities maintained upon platforms in natural or other bodies of water, including so-called "off shore drilling platforms". In conducting operations at these platforms industrial streams are developed (often referred to as "produced water") which by virtue of the processes conducted contain comparatively large quantities of mercury and various organic contaminants, including those mentioned above.

These contaminants must be partially or entirely removed from the industrial streams before such streams can be safely discharged. It will, of course, be understood that this is indeed merely one among very numerous examples of aqueous sources of polluting mercury and organic compounds which are of particular interest for the present invention.

Precipitating agents and flocculants have in the past been extensively used in batch operations for removal of pollutants, especially when colloidal suspensions and emulsions are involved. Precipitating agents are also often used by forming insoluble salts. In the case of semi-soluble organic compounds such as phenols and halogenated hydrocarbons, adsorbents such as activated carbon are among the most common materials used. Large amounts of such materials are often required due to desorption from the carbon because of the relative solubility of these compounds. Phenols and halogenated hydrocarbons are examples of organic materials which behave as organic acids under appropriate conditions. The present invention is in part directed at utilizing these characteristics of acidic organics, such as those mentioned, in order to remove same from the aqueous media in which they are present, and by use of a continuous process as opposed to batch processes.

Although mercury is a naturally occurring element that is present throughout the environment, direct exposure to mercury is harmful to people and wildlife. Power plants and other industrial sources release mercury pollution into the air. In the U.S., coal-fired power plants are the largest source of man-made mercury emissions to the air, accounting for approximately 40% of all mercury emissions. Once in the air, rain and snow deposit mercury into water bodies. Once in the water, mercury bioaccumulates in fish. People and wildlife are exposed to mercury primarily through consuming contaminated fish. Exposure to mercury can lead to toxicological effects in animals and humans, such as neurological and kidney disorders. The most sensitive populations are pregnant woman and their unborn children.

With respect to removal of mercury from aqueous systems such as the mentioned produced water, activated carbon is currently one of the most established mercury control technologies. Among other things different forms of mercury absorb at different rates, in consequence of which activated carbon is not very efficient at removing elemental mercury. Chemical reduction and air stripping has also been used as a low concentration mercury treatment concept for water containing Hg(II). The process consists of dosing the water with low levels of stannous chloride [Sn(II)] to convert the mercury to elemental mercury ($Hg^0$). $Hg^0$ can then be removed from the water by air stripping or sparging. Also known is a process based on photochemical oxidation. This has chiefly been known for use in treating flue gas wherein ultraviolet (UV) light is introduced into the flue gas, to convert elemental mercury to an oxidized form (i.e. mercuric oxide, mercurous sulfate, and mercurous chloride). Once in the oxidized form, mercury can be collected in existing air pollution control devices such as wet $SO_2$ scrubbers, electrostatic precipitators, and baghouses (fabric filters).

None of the foregoing techniques, however, have been fully successful in treating aqueous systems of the type with which the present invention is concerned.

SUMMARY OF INVENTION

In accordance with the present invention a method is disclosed for removing from an aqueous system which is contaminated with: (1) mercury present as colloids, ions and/or organically bound compounds, and (2) hydrocarbons solubilized, dispersed, and/or emulsified in the said system. A typical aqueous system to which the invention is applicable is so-called "produced water". It will, incidentally, be clear from this example of an aqueous system amenable to treatment by the present invention, that the term "aqueous system" as used herein not only encompasses the bulked mass of liquid in such a system, but as well the aqueous vapors that may be associated therewith and are characterized by dispersed fine aqueous droplets.

Pursuant to the invention, the aqueous system to be treated is passed successively through three filtration stages. The first filtration stage is provided with absorption media which effects reduction/removal of dispersed organically bound mercury species and of the dispersed and partially dissolved hydrocarbon phases, as well as of some colloidal mercury and other dissolved metallic species. The second filtration stage utilizes a salt modified reticulated granular filtration media for reduction/removal of slightly dissolved hydrocarbon phases, mercury in colloidal and ionic form, and other dissolved metals. The third filtration stage is a polishing stage, which serves to further reduce by electroless or voltaic reduction residual elemental mercury and/or residual colloidal and ionic mercury. At this third stage metallic mercury is incorporated into a metallic matrix from which the mercury may preferably be recovered.

The first filtration stage preferably comprises a fluid pervious filtration media which has been infused with an absorption composition comprising a homogeneous thermal reaction product of an oil component selected from the group consisting of glycerides, fatty acids, alkenes and alkynes, and a methacrylate or acrylate polymer component, whereby the removed contaminants are immobilized at the media.

At the second filtration stage the aqueous system is preferably contacted with a reticulated granular media comprised of a natural zeolite, carbon impregnated with the same absorbent composition specified for the first filtration stage, and granular activated carbon (GAC). The mechanism at this stage follows a reactive adsorption principle, which is facilitated by the ability of the natural zeolite to maintain a constant pH conducive to Lewis Acid Base interactions and precipitation of ionic and low molecular weight organo-mercury compounds. The said media has preferably been modified by a suitable salt such as a sulfate, phosphate and/or nitrate of a period I or period II alkali and or alkaline earth metal. The natural zeolite is activated in the presence of contamination and provides a gradual release of ions into an aqueous system such as produced water/vapor which causes precipitation of organically bound and ionic mercury. The impregnated carbon and the GAC protect the zeolite activator from soluble and semisoluble organics and also filters out the precipitates from solution.

The third filtration stage comprises an electrically conductive metallic matrix, the metal having an electromotive series position or an electrovoltaic potential appropriate to effect the reduction of the residual mercury. Where the reduction is electroless, ionic mercury is selectively reduced and metallic mercury is incorporated into a fixed alloy matrix to form an amalgam. The matrix may comprise a metallic mesh, which further may be in the form of a fine braid. The matrix may be disposed directly in a canister having an inlet and outlet, or the matrix may be incorporated into a plurality of tubes inside a larger canister, as in the second stage filter. Where the tubes or other containers are vertically disposed, the interstices present at the braided matrix can enable the depositing mercury upon the braid becoming saturated to result in the excess mercury flowing down the braid by a capillary or wicking action, enabling it to be recovered at an underlying receptacle or reservoir.

BRIEF DESCRIPTION OF DRAWINGS

The invention is diagrammatically illustrated by way of example in the drawings appended hereto in which.

DESCRIPTION OF PREFERRED EMBODIMENT

Figure 1:
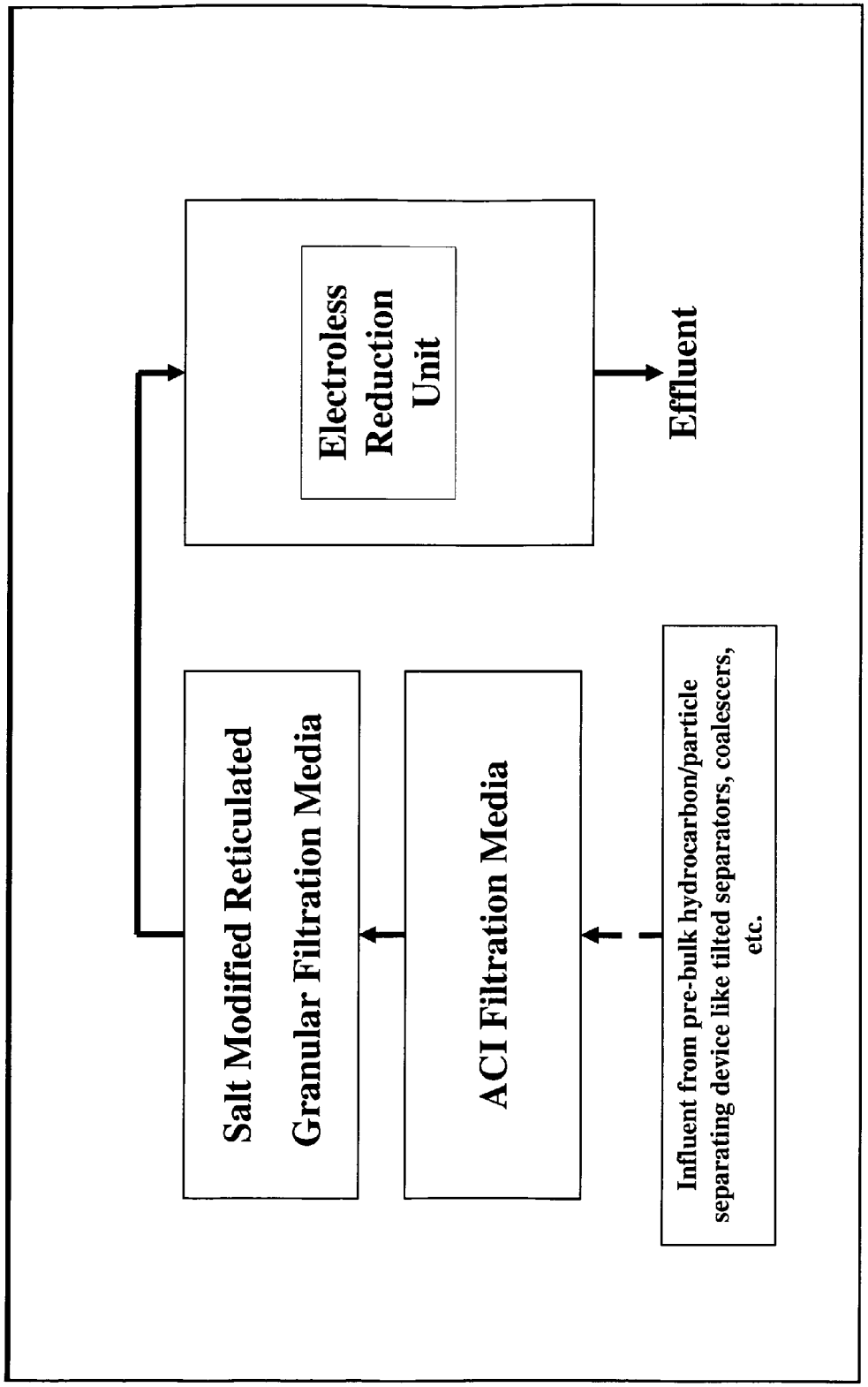
FIG. 1 is a schematic block diagram of a filtering system in which the present invention may be practiced.
Figure 2:
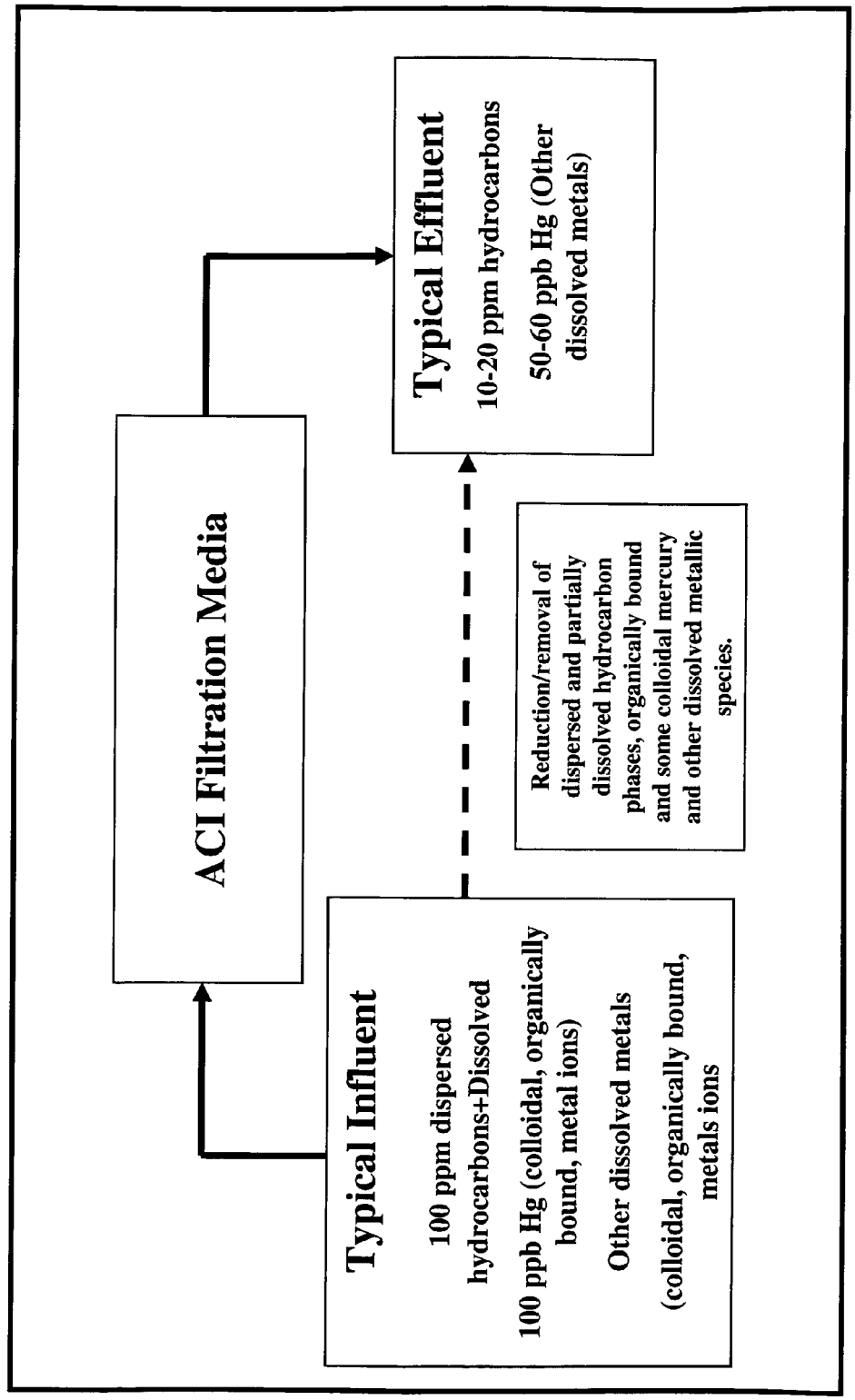
FIG. 2 is a schematic block diagram illustrating a typical arrangement for the stage 1 filtration portion of the system shown in FIG. 1.

Referring to the schematic block diagrams of FIGS. 1 and 2, the general method used in practice of the invention is schematically set forth. For purposes of illustration a contaminated stream or influent to be treated in accordance with the invention may illustratively be assumed to be one of produced water resulting from an off-shore oil well operation as has been previously discussed. The stream to be treated is characterized by the inclusion of (1) mercury present as colloids, ions or organically bound compounds (other dissolved metals may also be present); and (2) hydrocarbons solubilized, dispersed, or emulsified in the said media. As to item (2), these include acidic organic compounds, which are a main group of substances sought to be removed, such as phenols and halogenated hydrocarbons. Produced streams of the type referred to usually include additional contaminants, which may be important to remove before discharge into a body of water, notably including oily hydrocarbons and the like. Typical levels of the contaminants in the influent are shown in the legend of FIG. 2, i.e. 100 ppm dispersed and dissolved hydrocarbons, and 100 ppb of mercury as colloidal, organically bound and/or metal ions.

In accordance with the invention the influent stream at stage 1 is thus passed through an absorption composition-infused filtration media (referred to for convenience herein as an "ACI filtration media") which acts to remove substantial quantities of both the mercury items (1) and the hydrocarbon components (2) mentioned. Thus as is shown in FIG. 2, the typical resultant effluent has been vastly reduced in contaminants, e.g. mercury has been reduces from 100 ppb to 50-60 ppb, and the hydrocarbons from levels of 100 ppm to 10-20 ppm.

The ACI filtration media preferably comprises a fluid pervious filtration media which has been infused with an absorption composition comprising a homogeneous thermal reaction product of an oil component selected from the group consisting of glycerides, fatty acids, alkenes and alkynes, and a methacrylate or acrylate polymer component, whereby the oily contaminants are immobilized at the media. Filtration media of this type are disclosed in detail in the present applicant's U.S. Pat. No. 6,190,010, the disclosure of which is incorporated herein by reference. As set forth in that U.S. patent, the media (which is infused) can comprise a non-woven polypropylene, paper, a porous ceramic, a porous metal, a mineral particulate such as vermiculite or perlite, or so forth.

The term "absorbent composition" as used herein is one of convenience for identifying the said compositions of my aforementioned patent, and will be used as well in referring to the compositions used in stage I of the present invention. The specific mechanism by which the noxious contaminants are removed from aqueous streams by conjunctive use of such "absorbent compositions" is not completely understood, and could include attachment and/or fixation of such contaminants by mechanisms which technically involve various physical and/or chemical interactions. The term "absorbent" as used herein is intended to encompass all of these possible mechanisms.

The absorbent compositions used herein in the ACI filtration media are also disclosed in the present inventor's U.S. Pat. Nos. 5,437,793; 5,698,139; and 5,837,146, and 5,961,823 (all of which disclosures are hereby incorporated by reference) They have extremely strong affinities for the aforementioned hydrocarbon and also have been found to have affinities for the mercury contaminants in water.

Figure 3:
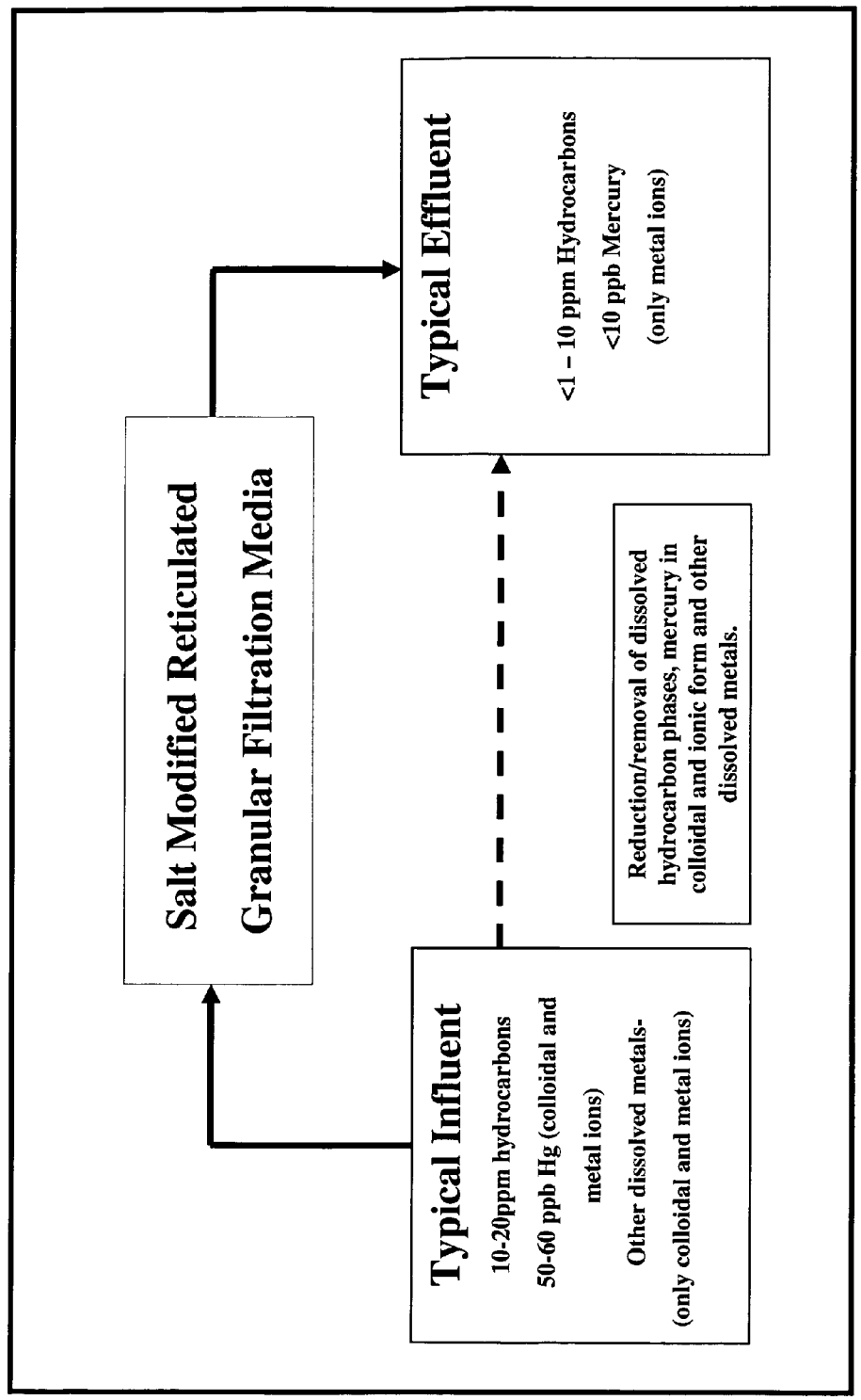
FIG. 3 is a schematic block diagram illustrating a typical arrangement for the stage 2 filtration portion of the system shown in FIG. 1.

Referring to FIGS. 1 and 3, the influent stream having been purified at stage 1 of the bulk of its hydrocarbon components and of substantial portions of its mercury based contaminants then passes to the second filtration stage, i.e. that based upon the salt modified reticulated granular filtration media. At the second filtration stage the aqueous system is preferably contacted with a reticulated granulated granular media comprised of a natural zeolite, an ACI filtration media such as carbon impregnated with the same impregnating absorbent composition specified for the first filtration stage, and granular activated carbon (GAC). Such media has preferably been modified by a suitable salt such as a sulfate, phosphate and/or nitrate of a period I or period II alkali metal and or alkaline earth metal. At this stage the very slightly soluble acidic acting organic compounds along with the mercury present in colloidal and/or ionic forms are removed by the media effecting acid based neutralization, stripping and reduction, enabling these pollutants to be removed from the waste stream. The media should preferably be capable of behaving as a base while at the same time having limited solubility in water so as to enable performing the neutralization in a continuous mode.

The streams to be treated by the invention at the second stage are preferably passed through a canister containing a plurality of replaceable tubes, the flow path being arranged to effect passage of the stream to be treated through such tubes. The interior of each tube is provided in series first with a section of the modifying salt or salts, followed by a section containing the reticulated granular filtration media. Additional sections of the tube may include a prefiltration section at the tube input, which contains a filtration media which has been infused with an absorption composition particularly suited for removal of oily components which may be present in the stream to be treated, and which would possibly foul the salt(s) section. The infused absorption media may be of the same type as discussed above for use in the first stage of the present invention. A post-filtration section at the output end of the tube may also be present, which again contains an infused absorption media of the type just indicated. The stream emerging from such a post-filtration section can be passed through a sodium carbonate or other ion exchange media, so that any remaining earth metal ions are exchanged for harmless sodium ions. As indicated in the legend in FIG. 3, the typical effluent then shows that mercury has been reduced to less than 10 ppb, and hydrocarbons to less than 1-10 ppm.

Figure 4:
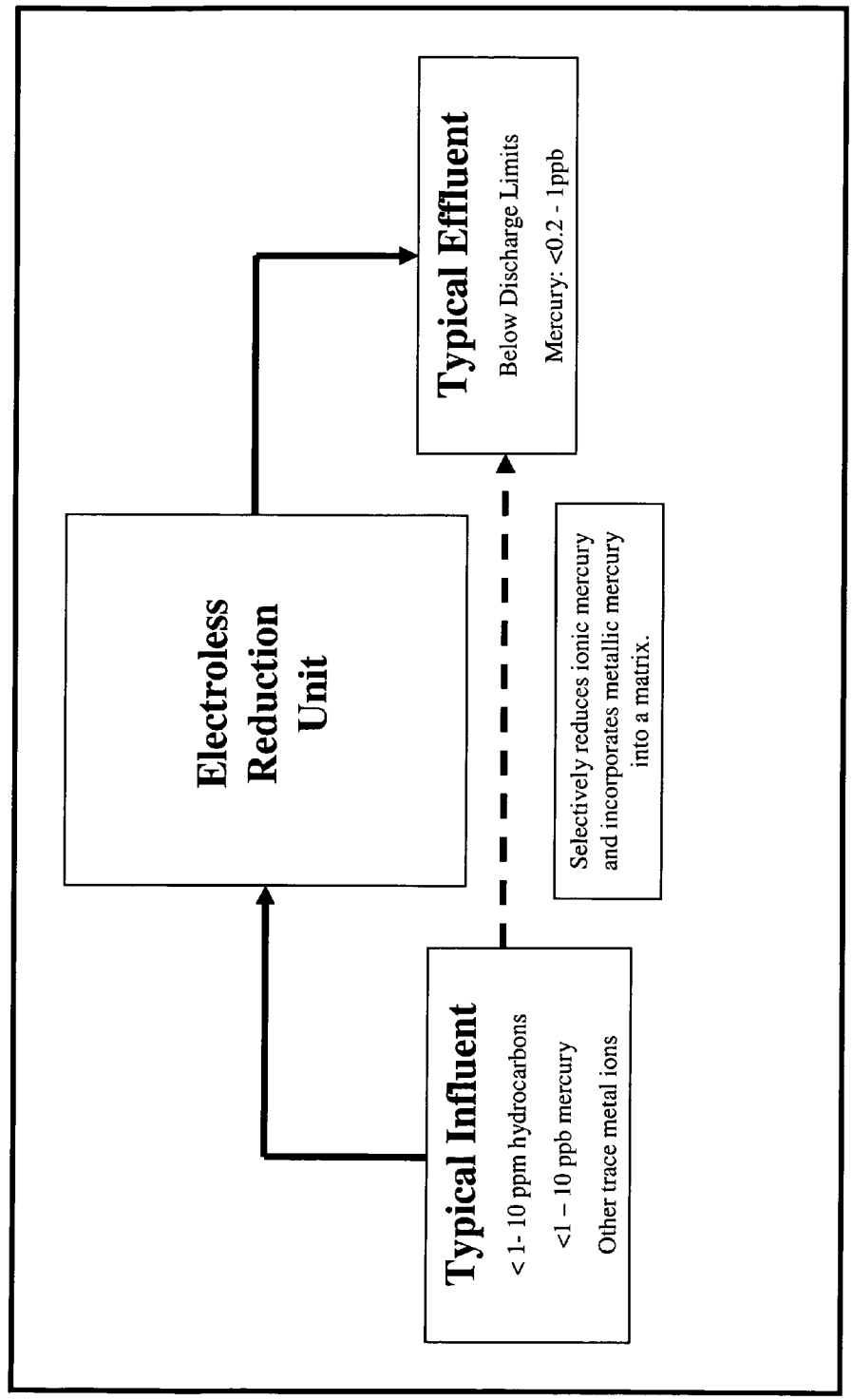
FIG. 4 is a schematic block diagram illustrating a typical arrangement for the stage 3 filtration portion of the system shown in FIG. 1.

Referring to FIG. 4, the effluent from stage 2 then becomes the influent stream for treatment in the aforementioned third (and final) filtration stage. The principal purpose of the final stage is to remove residual ionic and elemental mercury to less than 0.5 ppb. This level of purity is difficult for adsorptive media and ion exchange media to attain due to equilibrium effects. Electroless Reduction Technology eliminates the equilibrium effects by reducing and removing mercury. The final stage can be comprised of modular cartridges consisting of braided copper elements electroplated with a composition of precious metals. These elements serve to utilize the redox potential of ionic mercury and capture and amalgamate the reduced elemental mercury. The braiding allows for directional extraction and collection by exploiting the surface tension of metallic mercury.

The basic mechanisms involved are:

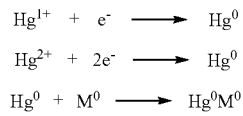

$M^0$ - Can be comprised of Au, Pt, Rh, Cu and other metals

Accordingly at this polishing stage, electroless or voltaic reduction are used to remove residual elemental mercury and/or residual colloidal and ionic mercury. The third filtration stage comprises an electrically conductive metallic matrix, the metal of which has an electromotive series position or an electrovoltaic potential appropriate to effect the reduction of the residual mercury. Where the reduction is electroless, ionic mercury is selectively reduced and metallic mercury is incorporated into a fixed alloy matrix to form an amalgam. The matrix may comprise a metallic mesh, which further may be in the form of a fine braid. Such braid may for example consist of braided copper coil which is electroplated with silver and gold. This matrix material will readily amalgamate elemental mercury. The matrix may be disposed directly in a canister having an inlet and outlet for the stream being treated, with the matrix being positioned in the canister to be in the flow path of the stream. Similarly the matrix may be incorporated into a plurality of tubes inside a larger canister, as in the second stage filter. An arrangement of this geometrical type is shown in FIG. 5 of the applicant's U.S. Pat. No. 7,264,722, except of course that the tubes there are associated with absorbents, not with metallic matrices for effecting reduction of mercury. Where the tubes or other containers are vertically disposed, the interstices present at the braided matrix can enable the depositing mercury upon the braid becoming saturated to result in the excess mercury flowing down the braid by a capillary or wicking action, enabling it to be recovered at an underlying receptacle or reservoir.

The present invention is further illustrated by the following Examples, which are indeed to be considered as merely exemplary and not delimitative of the invention otherwise described:

Examples I and II

Two samples of produced water were treated in the filtration system of the present invention. The samples were subjected to analysis as raw inputs and after being subjected to the method of the invention, i.e. to filtration by successive treatment at all three stages of the system of FIG. 1. For comparison the samples were also analyzed after filtration using various combinations of the stages of the present filtration system. In all instances the analysis were conducted using EPA method 1664. The results of these tests are shown in the below Table. The marked reductions in all of the contaminants will be evident. Particularly to be noted is the vast reduction in mercury, including the extremely effective action of stage 2 and the further polishing effect achieved after passing through stage 3, i.e. the electroless reduction stage. Note too here that where the electroless reduction stage is used alone the mercury reduction is very small, and thus it will be evident from this and the remaining data that a truly synergistic effect has been achieved by use in sequence of the three stages pursuant to the invention.

|  |  | Example I | | | | | | Example II | | | | | |
| --- | --- | --- | --- | --- | --- | --- | --- | --- | --- | --- | --- | --- | --- |
|  |  | Raw | ER only | After ACI | ACI and ER | ACI and SMRGM | ACI, SMRGM and ER | Raw | ER only | After ACI | ACI and ER | ACI and SMRGM | ACI, SMRGM and ER |
| O&G | ppm | 26.1 | NA | 9.9 | NA | ND | ND | 24.8 | NA | 8.7 | NA | ND | ND |
| SVOC | ppm | 157 | NA | 75 | NA | 0.044 | 0.044 | 56 | NA | 67.8 | NA | 0.087 | 0.087 |
| VOC | ppm | 36 | NA | 25 | NA | ND | ND | 36 | NA | 22 | NA | ND | ND |
| Hg | ppb | 63.6 | 55 | 23 | 22 | 1.1 | 0.46 | 41 | 37 | 17.1 | 17.3 | 1.1 | 0.46 |
| Total Organics | ppm | 219.1 |  |  |  |  |  | 116.8 |  |  |  |  |  |

O&G = oil and gas;
SVOC = semi-volatile organic compounds;
VOC = volatile organic compounds;
SMRGM = salt modified reticulated granular media;
ER = electroless reduction While the present invention has been set forth in terms of specific embodiments thereof, the instant disclosure is such that numerous variations upon the invention are now enabled to those skilled in the art, which variations yet reside within the scope of the present teaching. Accordingly, the invention is to be construed by broadly interpreting the scope and spirit of the present disclosure.

The invention claimed is:

1. A method for removing from aqueous media contaminated with: (1) mercury present as colloids, ions or organically bound compounds, and (2) hydrocarbons solubilized, dispersed, or emulsified in the said media; comprising:

passing the said media in successive order through (a) a first filtration stage comprising an absorption media which effects reduction/removal of dispersed organically bound mercury species, colloidal mercury, and dispersed and partially dissolved hydrocarbon phases, said first stage comprising a fluid pervious filtration media which has been infused with an absorption composition comprising a homogeneous thermal reaction product of an oil component selected from the group consisting of glycerides, fatty acids, alkenes and alkynes, and a methacrylate or acrylate polymer component, whereby removed contaminants are immobilized at the media;

(b) a second filtration stage comprising a salt modified reticulated granular filtration media for reduction/removal of slightly dissolved hydrocarbon phases, and mercury in colloidal and ionic form; said salt being selected from one or more members of the group consisting of a sulfate, phosphate and/or nitrate of a period I or period II alkali metal or alkaline earth metal; and (c) a third filtration stage comprising an electroless or voltaic actuated electrically conductive metallic matrix for reducing residual ionic mercury by electroless or voltaic reduction, and for extracting the reduced mercury and residual elemental and/or colloidal mercury by collection at the matrix, the metal of said matrix having an electromotive series position or an electrovoltaic potential appropriate to effect the reduction of the residual ionic mercury.

2. A method in accordance with claim 1, wherein the aqueous media comprises produced water.

3. A method in accordance with claim 1, wherein the reduction is electroless, ionic mercury being selectively reduced and metallic mercury being incorporated into a fixed alloy matrix to form an amalgam.

4. A method in accordance with claim 3, wherein said matrix comprises a mesh.

5. A method in accordance with claim 4, wherein said mesh is braided.

6. A method in accordance with claim 5, wherein the braided mesh comprises braided copper coil which is electroplated with silver and gold.

* * * * *